(12) United States Patent  (10) Patent No.: US 8,192,474 B2
Levinson  (45) Date of Patent: Jun. 5, 2012

(54) TISSUE TREATMENT METHODS

(75) Inventor: Mitchell Levinson, Pleasanton, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 1179 days.

(21) Appl. No.: 11/558,046

(22) Filed: Nov. 9, 2006

(65) Prior Publication Data

US 2008/0077202 A1    Mar. 27, 2008

(51) Int. Cl.
*A61F 7/00* (2006.01)
(52) U.S. Cl. ......... 607/96; 607/100; 607/108; 607/112
(58) Field of Classification Search ............. 607/100, 607/108, 112
See application file for complete search history.

(56) References Cited

U.S. PATENT DOCUMENTS

| | | |
|---|---|---|
| 889,810 A | 6/1908 | Robinson |
| 2,516,491 A | 7/1950 | Swastek |
| 3,093,135 A | 6/1963 | Hirschhorn |
| 3,132,688 A | 5/1964 | Nowak |
| 3,282,267 A | 11/1966 | Edius |
| 3,502,080 A | 3/1970 | Hirschhorn |
| 3,587,577 A | 6/1971 | Smirnov et al. |
| 3,591,645 A | 7/1971 | Selwitz |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Stumpf et al. |
| 3,942,519 A | 3/1976 | Shock |
| 3,948,269 A | 4/1976 | Zimmer |
| 3,986,385 A | 10/1976 | Johnston et al. |
| 4,140,130 A | 2/1979 | Storm, III |
| 4,178,429 A * | 12/1979 | Scheffer ............... 525/398 |
| 4,202,336 A | 5/1980 | van Gerven et al. |
| 4,266,043 A | 5/1981 | Fujii et al. |
| 4,381,009 A | 4/1983 | Del Bon et al. |
| 4,396,011 A | 8/1983 | Mack et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |

(Continued)

FOREIGN PATENT DOCUMENTS

CN    1511503 A    7/2004

(Continued)

OTHER PUBLICATIONS

U.S. Appl. No. 11/435,502, filed May 17, 2006, Levinson.

(Continued)

*Primary Examiner* — Roy Gibson
*Assistant Examiner* — Kaitlyn Smith
(74) *Attorney, Agent, or Firm* — Perkins Coie LLP

(57) ABSTRACT

Methods are provided herein for affecting a region of a subject's body, comprising exposing the region to a cooling element under conditions effective to cool subcutaneous adipose tissue in said region; and increasing the blood flow rate to the cooled tissue by exposing the tissue to an energy source. Methods are also provided for treating subcutaneous adipose tissue in a region of a subject's body, comprising exposing said region to a cooling element under conditions effective to cool said tissue; and exposing the tissue to an energy source to increase the blood flow rate to the cooled tissue, thereby stimulating reperfusion in, and/or causing an ischemia-reperfusion injury to, the cooled tissue.

25 Claims, 9 Drawing Sheets

U.S. PATENT DOCUMENTS

| | | | |
|---|---|---|---|
| 4,585,002 A | 4/1986 | Kissin | |
| 4,603,076 A | 7/1986 | Bowditch et al. | |
| 4,614,191 A | 9/1986 | Perler | |
| 4,644,955 A | 2/1987 | Mioduski | |
| 4,664,110 A | 5/1987 | Schanzlin | |
| 4,700,701 A | 10/1987 | Montaidi | |
| 4,718,429 A | 1/1988 | Smidt et al. | |
| 4,741,338 A * | 5/1988 | Miyamae | 607/112 |
| 4,764,463 A | 8/1988 | Mason et al. | |
| 4,802,475 A | 2/1989 | Weshahy et al. | |
| 4,832,022 A | 5/1989 | Tjulkov et al. | |
| 4,846,176 A | 7/1989 | Golden | |
| 4,850,340 A | 7/1989 | Onishi | |
| 4,869,250 A | 9/1989 | Bitterly | |
| 4,880,564 A | 11/1989 | Abel | |
| 4,906,463 A | 3/1990 | Cleary et al. | |
| 4,930,317 A | 6/1990 | Klein | |
| 4,961,422 A | 10/1990 | Marchosky et al. | |
| 4,962,761 A | 10/1990 | Golden | |
| 4,990,144 A | 2/1991 | Blott | |
| 5,007,433 A | 4/1991 | Hermsdorffer et al. | |
| 5,018,521 A * | 5/1991 | Campbell | 607/98 |
| 5,065,752 A | 11/1991 | Sessions et al. | |
| 5,069,208 A | 12/1991 | Noppel et al. | |
| 5,084,671 A | 1/1992 | Miyata et al. | |
| 5,108,390 A | 4/1992 | Potocky et al. | |
| 5,119,674 A | 6/1992 | Nielsen et al. | |
| 5,143,063 A | 9/1992 | Fellner | |
| 5,148,804 A | 9/1992 | Hill et al. | |
| 5,169,384 A | 12/1992 | Bosniak et al. | |
| 5,197,466 A | 3/1993 | Marchosky et al. | |
| 5,207,674 A | 5/1993 | Hamilton | |
| 5,221,726 A | 6/1993 | Dabi et al. | |
| 5,264,234 A | 11/1993 | Windhab et al. | |
| 5,277,030 A | 1/1994 | Miller | |
| 5,314,423 A | 5/1994 | Seney | |
| 5,330,745 A | 7/1994 | McDow | |
| 5,334,131 A | 8/1994 | Omandam et al. | |
| 5,336,616 A | 8/1994 | Livesey et al. | |
| 5,339,541 A | 8/1994 | Owens et al. | |
| 5,342,617 A | 8/1994 | Gold | |
| 5,351,677 A | 10/1994 | Kami et al. | |
| 5,427,772 A | 6/1995 | Hagan | |
| 5,433,717 A | 7/1995 | Rubinsky et al. | |
| 5,456,703 A | 10/1995 | Beeuwkes, III | |
| 5,472,416 A | 12/1995 | Blugerman et al. | |
| 5,497,596 A | 3/1996 | Zatkulak | |
| 5,505,726 A | 4/1996 | Meserol | |
| 5,507,790 A | 4/1996 | Weiss | |
| 5,514,105 A | 5/1996 | Goodman, Jr. et al. | |
| 5,514,170 A | 5/1996 | Mauch | |
| 5,531,742 A | 7/1996 | Barken | |
| 5,562,604 A | 10/1996 | Yablon et al. | |
| 5,571,801 A | 11/1996 | Segall et al. | |
| 5,603,221 A | 2/1997 | Maytal | |
| 5,628,769 A | 5/1997 | Saringer | |
| 5,647,868 A | 7/1997 | Chinn | |
| 5,650,450 A | 7/1997 | Lovette et al. | |
| 5,651,773 A | 7/1997 | Perry et al. | |
| 5,654,279 A | 8/1997 | Rubinsky | |
| 5,654,546 A | 8/1997 | Lindsay | |
| 5,660,836 A | 8/1997 | Knowlton | |
| 5,672,172 A | 9/1997 | Zupkas | |
| 5,733,280 A | 3/1998 | Avitall | |
| 5,741,248 A | 4/1998 | Stern et al. | |
| 5,746,736 A | 5/1998 | Tankovich | |
| 5,755,663 A | 5/1998 | Larsen et al. | |
| 5,755,753 A | 5/1998 | Knowlton | |
| 5,759,182 A | 6/1998 | Varney et al. | |
| 5,759,764 A | 6/1998 | Polovina | |
| 5,769,879 A | 6/1998 | Richards et al. | |
| 5,785,955 A | 7/1998 | Fischer | |
| 5,817,050 A | 10/1998 | Klein | |
| 5,830,208 A | 11/1998 | Muller | |
| 5,833,685 A | 11/1998 | Tortal et al. | |
| 5,844,013 A | 12/1998 | Kenndoff et al. | |
| 5,871,524 A | 2/1999 | Knowlton | |
| 5,871,526 A | 2/1999 | Gibbs et al. | |
| 5,895,418 A | 4/1999 | Saringer et al. | |
| 5,901,707 A | 5/1999 | Gonçalves et al. | |
| 5,902,256 A | 5/1999 | Benaron | |
| 5,919,219 A | 7/1999 | Knowlton | |
| 5,948,011 A | 9/1999 | Knowlton | 607/101 |
| 5,964,092 A | 10/1999 | Tozuka et al. | |
| 5,964,749 A | 10/1999 | Eckhouse et al. | |
| 5,967,976 A | 10/1999 | Larsen et al. | |
| 5,986,167 A | 11/1999 | Arteman et al. | |
| 6,017,337 A | 1/2000 | Pira | |
| 6,023,932 A | 2/2000 | Johnston et al. | |
| 6,032,675 A | 3/2000 | Rubinsky | |
| 6,039,694 A | 3/2000 | Larson et al. | |
| 6,041,787 A | 3/2000 | Rubinsky | |
| 6,049,927 A | 4/2000 | Thomas et al. | |
| 6,051,159 A | 4/2000 | Hao et al. | |
| 6,074,415 A | 6/2000 | Der Ovanesian | |
| 6,093,230 A | 7/2000 | Johnson, III et al. | |
| 6,102,885 A | 8/2000 | Bass | |
| 6,120,519 A | 9/2000 | Weber et al. | |
| 6,241,753 B1 | 6/2001 | Knowlton | |
| 6,264,649 B1 | 7/2001 | Whitcroft et al. | |
| 6,273,884 B1 | 8/2001 | Altshuler et al. | |
| 6,290,988 B1 | 9/2001 | Van Vilsteren et al. | |
| 6,311,090 B1 | 10/2001 | Knowlton | |
| 6,311,497 B1 | 11/2001 | Chung | |
| 6,350,276 B1 | 2/2002 | Knowlton | |
| 6,354,297 B1 | 3/2002 | Eiseman | |
| 6,357,907 B1 | 3/2002 | Cleveland et al. | |
| 6,377,854 B1 | 4/2002 | Knowlton | |
| 6,377,855 B1 | 4/2002 | Knowlton | |
| 6,381,497 B1 | 4/2002 | Knowlton | |
| 6,381,498 B1 | 4/2002 | Knowlton | |
| 6,387,380 B1 | 5/2002 | Knowlton | |
| 6,405,090 B1 | 6/2002 | Knowlton | |
| 6,413,255 B1 | 7/2002 | Stern | 606/41 |
| 6,425,912 B1 | 7/2002 | Knowlton | |
| 6,426,445 B1 | 7/2002 | Young et al. | |
| 6,430,446 B1 | 8/2002 | Knowlton | |
| 6,438,424 B1 | 8/2002 | Knowlton | |
| 6,438,964 B1 | 8/2002 | Giblin | |
| 6,453,202 B1 | 9/2002 | Knowlton | |
| 6,458,888 B1 | 10/2002 | Hood et al. | |
| 6,461,378 B1 | 10/2002 | Knowlton | |
| 6,470,216 B1 | 10/2002 | Knowlton | |
| 6,471,693 B1 | 10/2002 | Carroll et al. | |
| 6,494,844 B1 | 12/2002 | Van Bladel et al. | |
| 6,519,964 B2 | 2/2003 | Bieberich | |
| 6,523,354 B1 | 2/2003 | Tolbert | |
| 6,527,765 B2 | 3/2003 | Kalman et al. | |
| 6,544,248 B1 | 4/2003 | Bass | |
| 6,548,297 B1 | 4/2003 | Kuri-Harcuch et al. | |
| 6,551,349 B2 | 4/2003 | Lasheras et al. | |
| 6,569,189 B1 | 5/2003 | Augustine et al. | |
| 6,592,577 B2 | 7/2003 | Abboud et al. | |
| 6,605,080 B1 | 8/2003 | Altshuler et al. | |
| 6,626,854 B2 | 9/2003 | Friedman et al. | |
| 6,635,053 B1 | 10/2003 | Lalonde et al. | |
| 6,645,162 B2 | 11/2003 | Friedman et al. | |
| 6,645,229 B2 | 11/2003 | Matsumura et al. | |
| 6,648,904 B2 | 11/2003 | Altshuler et al. | |
| 6,699,266 B2 | 3/2004 | Lachenbruch et al. | |
| 6,718,785 B2 | 4/2004 | Bieberich | |
| 6,741,895 B1 | 5/2004 | Gafni et al. | |
| 6,746,474 B2 | 6/2004 | Saadat | |
| 6,749,624 B2 | 6/2004 | Knowlton | |
| 6,764,502 B2 | 7/2004 | Bieberich | |
| 6,789,545 B2 | 9/2004 | Littrup et al. | |
| 6,820,961 B2 | 11/2004 | Johnson | |
| 6,821,274 B2 | 11/2004 | McHale et al. | |
| 6,840,955 B2 | 1/2005 | Ein | |
| 6,878,144 B2 | 4/2005 | Altshuler et al. | |
| 6,904,956 B2 | 6/2005 | Noel | |
| 6,918,903 B2 | 7/2005 | Bass | |
| 6,942,022 B2 | 9/2005 | Blangetti et al. | |
| 6,945,942 B2 | 9/2005 | Van Bladel et al. | |
| 6,948,903 B2 | 9/2005 | Ablabutyan et al. | |
| 7,005,558 B1 | 2/2006 | Johansson et al. | |
| 7,022,121 B2 | 4/2006 | Stern et al. | |

| | | |
|---|---|---|
| 7,037,326 B2 | 5/2006 | Lee |
| 7,077,858 B2 | 7/2006 | Fletcher et al. |
| 7,081,111 B2 | 7/2006 | Svaasand et al. |
| 7,096,204 B1 | 8/2006 | Chen et al. |
| 7,112,712 B1 | 9/2006 | Ancell |
| 7,115,123 B2 | 10/2006 | Knowlton |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,713,266 B2 | 5/2010 | Elkins et al. |
| 7,854,754 B2 | 12/2010 | Ting et al. |
| 2001/0039439 A1 | 11/2001 | Elkins et al. |
| 2001/0045104 A1 | 11/2001 | Bailey et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0103520 A1 | 8/2002 | Latham |
| 2002/0117293 A1 | 8/2002 | Campbell |
| 2002/0151887 A1 | 10/2002 | Stern et al. |
| 2002/0188286 A1 | 12/2002 | Quijano et al. |
| 2003/0055414 A1* | 3/2003 | Altshuler et al. ............... 606/9 |
| 2003/0069618 A1* | 4/2003 | Smith et al. .................. 607/100 |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0125649 A1 | 7/2003 | McIntosh et al. |
| 2003/0220674 A1 | 11/2003 | Anderson et al. |
| 2003/0236487 A1 | 12/2003 | Knowlton |
| 2004/0006328 A1 | 1/2004 | Anderson et al. |
| 2004/0009936 A1 | 1/2004 | Tang et al. |
| 2004/0030332 A1 | 2/2004 | Knowlton |
| 2004/0034341 A1* | 2/2004 | Altshuler et al. ............... 606/3 |
| 2004/0039312 A1 | 2/2004 | Hillstead et al. ............... 601/2 |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0093042 A1 | 5/2004 | Altshuler et al. |
| 2004/0104012 A1 | 6/2004 | Zhou et al. |
| 2004/0162596 A1 | 8/2004 | Altshuler et al. |
| 2004/0199226 A1 | 10/2004 | Shadduck |
| 2004/0210214 A1 | 10/2004 | Knowlton |
| 2004/0210287 A1 | 10/2004 | Greene |
| 2004/0259855 A1 | 12/2004 | Anderson et al. |
| 2005/0049661 A1 | 3/2005 | Koffroth |
| 2005/0154431 A1 | 7/2005 | Quistgaard et al. ............. 607/96 |
| 2005/0159986 A1 | 7/2005 | Breeland et al. |
| 2005/0182462 A1 | 8/2005 | Chornenky et al. |
| 2005/0187597 A1 | 8/2005 | Vanderschuit |
| 2005/0222565 A1 | 10/2005 | Manstein |
| 2005/0251120 A1 | 11/2005 | Anderson et al. ............... 606/20 |
| 2006/0030778 A1 | 2/2006 | Mendlein et al. |
| 2006/0036300 A1 | 2/2006 | Kreindel |
| 2006/0074313 A1 | 4/2006 | Slayton et al. |
| 2006/0079852 A1 | 4/2006 | Bubb et al. |
| 2006/0122509 A1 | 6/2006 | Desilets ........................ 600/439 |
| 2006/0200063 A1 | 9/2006 | Munro et al. |
| 2006/0234899 A1 | 10/2006 | Nekmard et al. |
| 2006/0270745 A1 | 11/2006 | Hunt et al. |
| 2006/0293734 A1 | 12/2006 | Scott et al. |
| 2007/0010861 A1 | 1/2007 | Anderson et al. |
| 2007/0032561 A1 | 2/2007 | Lin et al. |
| 2007/0129714 A1 | 6/2007 | Elkins et al. |
| 2007/0141265 A1 | 6/2007 | Thomson |
| 2007/0198071 A1 | 8/2007 | Ting et al. |
| 2007/0239075 A1 | 10/2007 | Rosenberg et al. |
| 2007/0249519 A1 | 10/2007 | Guha et al. |
| 2007/0255187 A1 | 11/2007 | Branch |
| 2007/0282249 A1 | 12/2007 | Quisenberry et al. |
| 2008/0046047 A1 | 2/2008 | Jacobs |
| 2008/0140371 A1 | 6/2008 | Warner |
| 2008/0183164 A1 | 7/2008 | Elkins et al. |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2010/0081971 A1 | 4/2010 | Allison |
| 2010/0280582 A1 | 11/2010 | Baker et al. |
| 2012/0022518 A1 | 1/2012 | Levinson |

FOREIGN PATENT DOCUMENTS

| | | |
|---|---|---|
| CN | 1741777 A | 3/2006 |
| CN | 1817990 A | 8/2006 |
| DE | 532976 C | 9/1931 |
| DE | 2851602 | 6/1980 |
| DE | 4213584 | 11/1992 |
| DE | 4224595 | 1/1994 |
| EP | 0263069 | 4/1988 |
| EP | 0397043 | 11/1990 |
| EP | 0406244 | 1/1991 |
| EP | 0598824 A1 | 6/1994 |
| GB | 2286660 | 8/1995 |
| GB | 2323659 A | 9/1998 |
| JP | 63076895 A | 4/1988 |
| JP | 03051964 A | 3/1991 |
| JP | 3259975 A | 11/1991 |
| JP | 4093597 A | 3/1992 |
| JP | 6282977 A | 10/1994 |
| JP | 7194666 A | 8/1995 |
| JP | 7268274 A | 10/1995 |
| JP | 09164163 A | 6/1997 |
| JP | 10216169 A | 8/1998 |
| JP | 10223961 A | 8/1998 |
| JP | 2000503154 A | 3/2000 |
| JP | 2002543668 A | 12/2002 |
| JP | 2004013600 A | 1/2004 |
| JP | 2005039790 A | 2/2005 |
| JP | 3655820 | 3/2005 |
| JP | 200565984 | 3/2005 |
| JP | 2005520608 A | 7/2005 |
| JP | 2005520608 T | 7/2005 |
| JP | 2006026001 A | 2/2006 |
| JP | 2006520949 A | 9/2006 |
| KR | 1020040094508 | 11/2004 |
| SU | 532976 | 11/1978 |
| TW | 0476644 | 2/2002 |
| WO | WO 96/36293 | 11/1996 |
| WO | WO 96/37158 | 11/1996 |
| WO | WO 97/05828 | 2/1997 |
| WO | WO 97/22262 | 6/1997 |
| WO | WO-9725798 A1 | 7/1997 |
| WO | WO 98/41157 | 9/1998 |
| WO | WO-9841156 A1 | 9/1998 |
| WO | WO 99/38469 | 8/1999 |
| WO | WO 00/44346 | 8/2000 |
| WO | WO-0065770 A1 | 11/2000 |
| WO | WO 02/05736 A2 | 1/2002 |
| WO | WO 02/102921 A1 | 12/2002 |
| WO | WO 03/078596 | 9/2003 |
| WO | WO-03078596 A2 | 9/2003 |
| WO | WO 2004/000098 A2 | 12/2003 |
| WO | WO-2004080279 A2 | 9/2004 |
| WO | WO-2005046540 A1 | 5/2005 |
| WO | WO-2006066226 | 6/2006 |
| WO | WO-2006127467 | 11/2006 |
| WO | WO-2007012083 A2 | 1/2007 |
| WO | WO-2007041642 A2 | 4/2007 |
| WO | WO-2010077841 A1 | 7/2010 |
| WO | WO-2010127315 A2 | 11/2010 |
| WO | WO-2012012296 A1 | 1/2012 |

OTHER PUBLICATIONS

U.S. Appl. No. 11/528,225, filed Sep. 26, 2006, Levinson et al.
U.S. Appl. No. 11/528,189, filed Sep. 26, 2006, Levinson et al.
U.S. Appl. No. 11/741,271, filed Apr. 27, 2007, Levinson et al.
U.S. Appl. No. 11/750,953, filed May 18, 2007, Rosen et al.
U.S. Appl. No. 11/777,992, filed Jul. 13, 2007, Levinson et al.
U.S. Appl. No. 11/777,995, filed Jul. 13, 2007, Levinson et al.
U.S. Appl. No. 11/777,999, filed Jul. 13, 2007, Levinson et al.
U.S. Appl. No. 11/778,001, filed Jul. 13, 2007, Levinson et al.
U.S. Appl. No. 11/778,003, filed Jul. 13, 2007, Levinson et al.
Ardevol "Cooling rates of tissue samples during freezing with liquid nitrogen" J. of Biochem and Biophysical Methods, 27, 77-86 (1993).

Bondei, E. et al., "Disorders of Subcutaneous Tissue (Cold Panniculitis)," *Dermatology in General Medicine*, Chapter 108, Section 16: 1333-1334, 1993.

Burge, S.M. et al., "Hair Follicle Destruction and Regeneration in Guinea Pig Skin after Cutaneous Freeze Injury," *Cryobiology*, 27(2): 153-163, 1990.

Duncan, W.C. et al., "Cold Panniculitis," *Arch. Derm.*, 94: 722-24, 1966.

Epstein, E.H. et al., "Popsicle Panniculitis," *The New England Journal of Medicine*, 282(17):966-67, 1970.

Gage "Current Progress in Cryosurgery" Cryobiology 25, 483-486 (1988).

Heller-Page et al., "Temperature-dependent skin disorders," Journal of the American Academy of Dermatology, 1988, vol. 18, No. 5, Pt 1, pp. 1003-1019.

Hemmingsson "Attenuation in Human Muscle and Fat Tissue in Vivo and in Vitro" Acta Radiologica Diagnosis 23, 149-151 (1982).

Henry et al., "Les Dermatoses Hivernales," Rev Med Liege, 1999, 54:11, 864-866.

Holman "Variation in cryolesion penetration due to probe size and tissue thermal conductivity" Ann. Thorac. Surg. 53, 123-126 (1992).

Hong et al., "Patterns of Ice Formation in Normal and Malignant Breast Tissue" Cryobiology 31, 109-120 (1994).

Kellum, R.E. et al., "Sclerema Neonatorum: Report of Case and Analysis of Subcutaneous and Epidermal-Dermal Lipids by Chromatographic Methods," *Arch. Derm.*, 97:372-80, 1968.

Koska, J. et al., "Endocrine Regulation of Subcutaneous Fat Metabolism During Cold Exposure in Humans," *Ann. N. Y. Acad, Sci.*, 967:500-05, 2002.

Laugier, et al., "In Vivo Results with a New Device for Ultrasonic Monitoring of Pig Skin Cryosurgery: The Echographic Cryprobe", The society for Investigative Dermatology, Inc., vol. 111 (2), Aug. 1998.

Maize, J.C., "Panniculitis," *Cutaneous Pathology*, Chapter 13: 327-344, 1998.

Malcom, G. et al., "Fatty Acid Composition of Adipose Tissue in Humans: Differences between Subcutaneous Sites," *Am. J. Clin. Nutr.*, 50(2): 288-91, 1989.

Moschella, S.L. et al., "Diseases of the Subcutaneous Tissue," *Derm.*, Section 2: 1169-1181, 1985.

Murphy, J.V. et al., "Frostbite: Pathogensesis and Treatment," *The Journal of Trauma: Injury, Infection, and Critical Care*, 48(1):171-178, 2000.

Nagore et al., "Lipoatrophia semicircularis—a traumatic panniculitis: Report of seven cases and review of the literature," Journal of the American Academy of Dermatology: pp. 879-881, 1998.

Pease "An Integrated Probe for Magnetic Resonance Imaging Monitored Skin Cryosurgery" Journal of Biomedical Engineering 117, 59-63, (1995).

Pech "Attenuation values, volume changes and artifacts in tissue due to freezing" Acta Radiologica 6, 779-782 (1987).

Phinney, S.D. et al., "Human Subcutaneous Adipose Tissue Shows Site-Specific Differences in Fatty Acid Composition," *Am. J. Clin. Nutr.*, 60: 725-29, 1994.

Rabi "Metabolic adaptations in brown adipose tissue of the hamster in extreme ambient temperatures" American Journal of Physiology 231, 153-160 (1976).

Renold, A.E., "Adipose Tissue," *Handbook of Physiology*, Chapter 15: 170-76, 1965.

Rubinsky "Cryosurgery: advances in the application of low temperatures to medicine" Int. J. Refrig. 190-199 (1991).

Shephard, "Adaptation to Exercise in the Cold," Sports Medicine, 1985, 2:59-71.

Winkler et al., "Gene Transfer in Laboratory Fish: Model Organisms for the Analysis of Gene Function," Transgenic Animals, 1997, pp. 387-395.

Young, H.E. et al., "Isolation of Embryonic Chick Myosatellite and Pluripotent Stem Cells," *J. Tiss. Cult. Meth.*, 14: 85-92, 1992.

International Search Report for Applicant: PCT/US2007/075935; Zeltiq Aesthetics, Inc; Date of Mailing: Apr. 10, 2008 (4 pages).

U.S. Appl. No. 12/196,246, filed Aug. 21, 2008, Levinson.

U.S. Appl. No. 12/275,002, filed Nov. 20, 2008, Martens.

U.S. Appl. No. 12/275,014, filed Nov. 20, 2008, Martens.

U.S. Appl. No. 12/337,544, filed Dec. 17, 2008, Alison.

Bohm et al., "Saline-enhanced radiofrequency ablation of breat tissue: an in vitro feasibility study," Invest Radiol, 2000, pp. 149-157, vol. 35—issue (3).

Disclosure re: "Method and Apparatus for Regional Fat Reduction Using Controlled and Sustained Cooling of Skin Surface".

Donski et al., "The Effects of Cooling no Experimental Free Flap Survival," Brit J Plas Surg, 1980, pp. 353-360, vol. 33.

Hale et al., "Influence of chronic heat exposure and prolonged food deprivation on excretion of mahnesium, phosphorus, calcium, hydrogen ion & ketones," Aerosp Med, 1968, pp. 919-926, vol. 39—issue (9).

International Search Report and Written Opinion for PCT/US2007/062508; Applicant: Juniper Medical, Inc.; Date of Mailing: Jul. 20, 2007, 13 pages.

International Search Report and Written Opinion for PCT/US2007/064016; Applicant Juniper Medical, Inc.; Date of Mailing: Jul. 20, 2007, 13 pages.

International Search Report and Written Opinion for PCT/US2007/064017; Applicant: Juniper Medical, Inc.; Date of Mailing: Oct. 26, 2007, 16 pages.

International Search Report and Written Opinion for PCT/US2007/064018; Applicant: Juniper Medical, Inc.; Date of Mailing: Jul. 26, 2007, 13 pages.

International Search Report and Written Opinion for PCT/US2007/067638; Applicant: Juniper Medical, Inc.; Date of Mailing: Jan. 10, 2008, 11 pages.

International Search Report and Written Opinion for PCT/US2007/069694; Applicant: Juniper Medical, Inc.; Date of Mailing: Nov. 23, 2007, 12 pages.

International Search Report and Written Opinion for PCT/US2007/083255; Applicant: Zeltiq Aesthetics, Inc.; Date of Mailing: Aug. 11, 2008, 8 pages.

International Search Report and Written Opinion for PCT/US2008/073930; Applicant: Zeltiq Aesthetics, Inc.; Date of Mailing: Nov. 7, 2008, 10 pages.

International Search Report for EP07758558.6; Applicant: Zeltiq Aesthetics, Inc.; Mailed on Jul. 20, 2007, 4 pages.

International Search Report for PCT/US2005/045988; (Apr. 25, 2006).

Kundu et al., "Breath acetone analyzer: diagnostic tool to monitor dietary fat loss," Clin Chem, 1993, pp. 87-92, vol. 39, issue (1).

Kundu et al., "Novel solid-phase assay of ketone bodies in urine," Clin Chem, 1991, pp. 1565-1569, vol. 37—issue (9).

Kuroda et al., "Thermal distribution of radio-frequency inductive hyperthermia using an inductive aperture-type applicator: evaluation of the effect of tumour size and depth," Med Biol Eng Comput, 1999, pp. 285-290, vol. 37—issue (3).

Levchenko, et al., "Effect of dehydration on lipid metabolism," WMJ, 1978, pp. 95-97, vol. 50—issue (1).

Lidagoster, MD et al., "Comparison of Autologous Fat Transfer in Fresh, Refridgerated, and Frozen Specimens: An Animal Model Presented," at the 16th Annual Meeting of the Northeastern Society of Plastic Surgeons: Burlington, VT, 1999, pp. 512-515.

Lvova, "Lipid levels and lipid peroxidation in frog tissues during hypothermia and hibernation," WMJ, 1990, pp. 65-70, vol. 62—issue (1).

Nagao et al., "Dietary diacylglycerol suppresses accumulation of body fat compared to triacylglycerol in men a double-blind controlled trial," J Nutr, 2000, pp. 792-797, vol. 130—issue (4).

Nielsen, "Thermoregulation in Rest and Exercise," Acta Phys Scan Supp, 1969, pp. 6-74, vol. 323.

Non-Final Office Action; U.S. Appl. No. 11/435,502; Date of Mailing: Jul. 17, 2009, 10 pages.

Peterson et al., "Bilateral Fat Necrosis of the Scrotum, Urology Service, Department of Surgery, Dermatology Service, Department of Medicine and Department of Pediatrics," Letterman Army Medical Center, Journal of Urology, 1976, pp. 825-826, vol. 116, The Williams & Wilkins Co.

Schoning, et al., "Experimental Frostbite: Freezing Times, Rewarming Times, and Lowest Temperatures of Pig Skin Exposed to Chilled Air," Cryobiology, 1990, pp. 189-193, 27.

U.S. Appl. No. 60/795,799, filed Apr. 28, 2006.

Coban, "Ischemia-Reperfusion Injury of Adipofascial Tissue: An Experimental Study Evaluating Early Histologic and Biochemical Alterations in Rats," *Mediators of Inflammation*, 2005, 5, 304-308.

Liu, A. Y.-C., et al., "Transient Cold Shock Induces the Heat Shock Response upon Recovery at 37° C. in Human Cells," *J. Biol. Chem.*, May 20, 1994, 269(20), 14768-14775.

Nishikawa, "Ultrastructural Changes and Lipid Peroxidation in Rat Adipomusculocutaneous Flap Isotransplants after Normothermic Storage and Reperfusion," *Transplantation*, 1992, 54, 795-801.

European Search Report, European Patent Application No. 10167756.5, Applicant: The General Hospital Corporation, Mailing Date: Aug. 31, 2010, 6 pages.

Final Office Action; U.S. Appl. No. 11/528,225; Date of Mailing: Dec. 29, 2010, 12 pages.

International Search Report and Written Opinion for PCT/US2010/033290; Applicant: Zeltiq Aesthetics, Inc.; Mailed on Feb. 25, 2011, 12 pages.

International Search Report and Written Opinion for PCT/US2011/022112; Applicant: Zeltiq Aesthetics, Inc.; Mailed on Mar. 18, 2011, 11 pages.

International Search Report and Written Opinion for PCT/US2011/022444; Applicant: Zeltiq Aesthetics, Inc., Mailed on Mar. 29, 2011, 14 pages.

Non-Final Office Action; U.S. Appl. No. 11/741,271; Date of Mailing: Jul. 12, 2010, 9 pages.

Non-Final Office Action; U.S. Appl. No. 12/942,852; Date of Mailing: Jun. 30, 2011, 10 pages.

Non-Final Office Action; U.S. Appl. No. 11/528,225; Date of Mailing: Aug. 3, 2011, 13 pages.

Wang et al., "Cryopreservation of cell/hydrogel constructs based on a new cell-assembling technique", Sep. 5, 2009, 40 pages.

Wharton et al., "Cold acclimation and cryoprotectants in a freeze-tolerant Antarctic nematode, *Panagrolaimus davidi*," Mar. 7, 2000, 2 pages.

Non-Final Office Action; U.S. Appl. No. 12/565,613; Date of Mailing: Sep. 23, 2011, 55 pages.

International Search Report for Application No. PCT/US2007/023492; Applicant: Zeltiq Aesthetics, Inc.; Date of Mailing: May 15, 2008 (2 pages).

Final Office Action; U.S. Appl. No. 10/391,221; Date of Mailing: Aug. 24, 2006, 4 pages.

Final Office Action; U.S. Appl. No. 11/016,196; Date of Mailing: Mar. 23, 2010, 12 pages.

Final Office Action; U.S. Appl. No. 11/435,502; Date of Mailing: Mar. 29, 2010, 11 pages.

International Search Report and Written Opinion for PCT/US2009/058088; Applicant: Zeltiq Aesthetics, Inc.; Date of Mailing: Nov. 20, 2009, 14 pages.

International Search Report and Written Opinion for PCT/US2009/067973; Applicant: Zeltiq Aesthetics, Inc.; Date of Mailing: Feb. 18, 2010, 10 pages.

Non-Final Office Action; U.S. Appl. No. 10/391,221; Date of Mailing: Jan. 25, 2006, 6 pages.

Non-Final Office Action; U.S. Appl. No. 10/391,221; Date of Mailing: May 30, 2007, 8 pages.

Non-Final Office Action; U.S. Appl. No. 10/391,221; Date of Mailing: Jul. 22, 2005, 6 pages.

Non-Final Office Action; U.S. Appl. No. 11/016,196; Date of Mailing: Apr. 22, 2008, 11 pages.

Non-Final Office Action; U.S. Appl. No. 11/016,196; Date of Mailing: Sep. 25, 2009, 8 pages.

Non-Final Office Action; U.S. Appl. No. 11/359,092; Mailed on Nov. 19, 2009, 13 pages.

Pre-Interview Office Action; U.S. Appl. No. 11/434,478; Date of Mailing: May 6, 2010, 4 pages.

Non-Final Office Action; U.S. Appl. No. 11/528,225; Date of Mailing: Apr. 12, 2010, 11 pages.

\* cited by examiner

TISSUE TREATMENT METHODS

FIELD OF THE INVENTION

The present invention relates generally to methods for treating mammalian tissue, to subcutaneous adipose tissue treatment methods, and particularly to those involving cooling of the tissue.

BACKGROUND OF THE INVENTION

Excess body fat increases the likelihood of developing various types of diseases such as heart disease, high blood pressure, osteoarthrosis, bronchitis, hypertension, diabetes, deep-vein thrombosis, pulmonary emboli, varicose veins, gallstones, hernias, and several other conditions.

In addition to being a serious health risk, excess body fat can also detract from personal appearance and athletic performance. For example, excess body fat can form cellulite, which causes an "orange peel" effect at the surface of the skin. Cellulite forms when subcutaneous fat protrudes into the dermis and creates dimples where the skin is attached to underlying structural fibrous strands. Cellulite and excessive amounts of fat are often considered to be unappealing. Thus, in light of the serious health risks and aesthetic concerns associated with excess fat, an effective way of controlling excess accumulation of body fat is urgently needed.

Liposuction is a method for selectively removing body fat to sculpt a person's body. Liposuction is typically performed by plastic surgeons and dermatologists using specialized surgical equipment that mechanically removes subcutaneous fat cells via suction. One drawback of liposuction is that it is a serious surgical procedure, and the recovery may be painful. Liposuction can have serious and occasionally even fatal complications. In addition, the cost for liposuction is usually substantial.

Conventional non-invasive treatments for removing excess body fat typically include topical agents, weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or negative reaction. Furthermore, fat loss in selective areas of a person's body cannot be achieved using general or systemic weight-loss methods.

Other non-invasive treatment methods include applying heat to a zone of subcutaneous lipid-rich cells. U.S. Pat. No. 5,948,011 discloses altering subcutaneous body fat and/or collagen by heating the subcutaneous fat layer with radiant energy while cooling the surface of the skin.

Another method of reducing subcutaneous fat cells is to cool the target cells as disclosed in U.S. Patent Publication No. 2003/0220674 or in U.S. Patent Publication No. 2005/0251120, the entire disclosures of which are incorporated herein. These publications disclose, among other things, reducing the temperature of lipid-rich subcutaneous fat cells to selectively affect the fat cells without damaging the cells in the epidermis. Although these publications provide promising methods and devices, several improvements for enhancing the implementation of these methods and devices would be desirable.

In medicine, ischemia is a restriction in blood supply, generally due to factors in the blood vessels, with resultant damage or dysfunction of tissue. Since oxygen is mainly bound to hemoglobin in red blood cells, insufficient blood supply causes tissue to become hypoxic, or, if no oxygen is supplied at all, anoxic. This can cause necrosis and cell death. Ischemia is a feature of heart diseases, transient ischemic attacks, cerebrovascular accidents, ruptured arteriovenous malformations, and peripheral artery occlusive disease. Tissues that are especially sensitive to inadequate blood supply include the heart, the kidneys, and the brain.

Restoration of blood flow after a period of ischemia is generally recognized to actually be more damaging than the ischemia itself. The absence of oxygen and nutrients from blood creates a condition in which the restoration of circulation results in inflammation and oxidative damage from the oxygen (i.e., reperfusion injury) rather than restoration of normal function. Reintroduction of oxygen also causes a greater production of damaging free radicals. With perfusion injury, necrosis can be greatly accelerated.

SUMMARY OF THE INVENTION

In one aspect, the present invention provides methods and devices that use ischemia-reperfusion injury to reduce or eliminate fat cells in the human body. Although it is generally considered desirable to minimize ischemia-reperfusion injury to cells in the human body, it is believed, while not intending to be bound by theory, that it is beneficial to effect ischemia-reperfusion injury in adipose tissue, thus enhancing adipose tissue necrosis or apoptosis.

In certain embodiments, the present invention thus provides methods for affecting a region of a subject's body, comprising exposing an epidermal layer in said region to a cooling element under conditions effective to cool subcutaneous adipose tissue in said region; and increasing the rate of blood flow to the cooled tissue by exposing the tissue to an energy source.

In another embodiment, the invention provides methods of treating subcutaneous adipose tissue in a region of a subject's body, comprising exposing said region to a cooling element under conditions effective to cool said tissue; and stimulating reperfusion in the cooled tissue by exposing the tissue to an energy source to increase the blood flow rate to the cooled tissue.

The present invention also provides methods of treating subcutaneous adipose tissue in a region of a subject's body, comprising exposing said region to a cooling element under conditions effective to cool said tissue; and causing an ischemia-reperfusion injury to the cooled tissue by exposing the tissue to an energy source to increase the blood flow rate to the cooled tissue.

In still another embodiment, the present invention provides cooling methods for selective reduction of lipid-rich cells in a region of a human subject's body, comprising applying a cooling element proximal to the subject's skin to reduce the temperature within a local region containing the lipid-rich cells sufficiently to selectively reduce the lipid-rich cells of said region, and concurrently therewith maintain the subject's skin at a temperature wherein non-lipid-rich cells proximate to the cooling element are not reduced; and subsequent to applying a cooling element, applying an energy source to the cooled tissue to thereby increase a rate of blood flow to the cooled tissue.

In another embodiment, the present invention provides methods for selective reduction of lipid-rich cells in a region of a human subject's body, comprising selectively causing vasoconstriction in adipose tissue; and subsequently stimulating reperfusion by applying an energy source to thereby increase blood flow to the region.

In still another embodiment, the present invention provides methods for selectively creating ischemia in lipid-rich cells in a region of a human subject's body, and subsequently stimulating reperfusion by applying an energy source to thereby increase the blood flow.

The figures are provided by way of example and are not intended to be limiting.

DETAILED DESCRIPTION OF ILLUSTRATIVE EMBODIMENTS

In one embodiment, the present invention provides methods for affecting a region of a subject's body, comprising exposing an epidermal layer in said region to a cooling element under conditions effective to cool subcutaneous adipose tissue in said region; and increasing the blood flow rate to the cooled tissue by exposing the tissue to an energy source.

In certain embodiments, the methods further comprise cycling at least one of the steps of exposing said region to a cooling element and increasing blood flow. For example, after a cycle of exposing said region to a cooling element and increasing blood flow, a step of exposing said region to a cooling element could be repeated. Alternatively, a step of increasing blood flow could be added.

In certain embodiments, the methods of the invention further comprise increasing vasoconstriction in the adipose tissue. This can be achieved by various mechanical, chemical means or certain cooling conditions. Certain drugs can be administered orally or injected into the adipose tissue to increase vasoconstriction. Epinephrine is an example of one vasoconstrictive drug that is commonly injected. Other examples include norepinephrine, catecholamines, epinephrine isoproterenol, dopamine, ephedrine, phenylephrine, amphetamine, metraminol, methoxamine, ergot alkaloids, ergonovine, methylergonavine, methysergide, and ergotamine. A mechanical means for increasing vasoconstriction would be by application of pressure to the region.

For purposes of this specification, "affecting" means affecting, disrupting, shrinking, disabling, destroying, removing, killing, or otherwise being altered. As mentioned above, cooling subcutaneous adipose tissue may result in disruption and eventual death of the adipocytes.

The term "subject," as used herein, includes any animal having blood, adipose tissue, and an epidermis. In preferred embodiments, the subject is a human or some other mammal, even more preferably a non-infant human.

Figure 1:
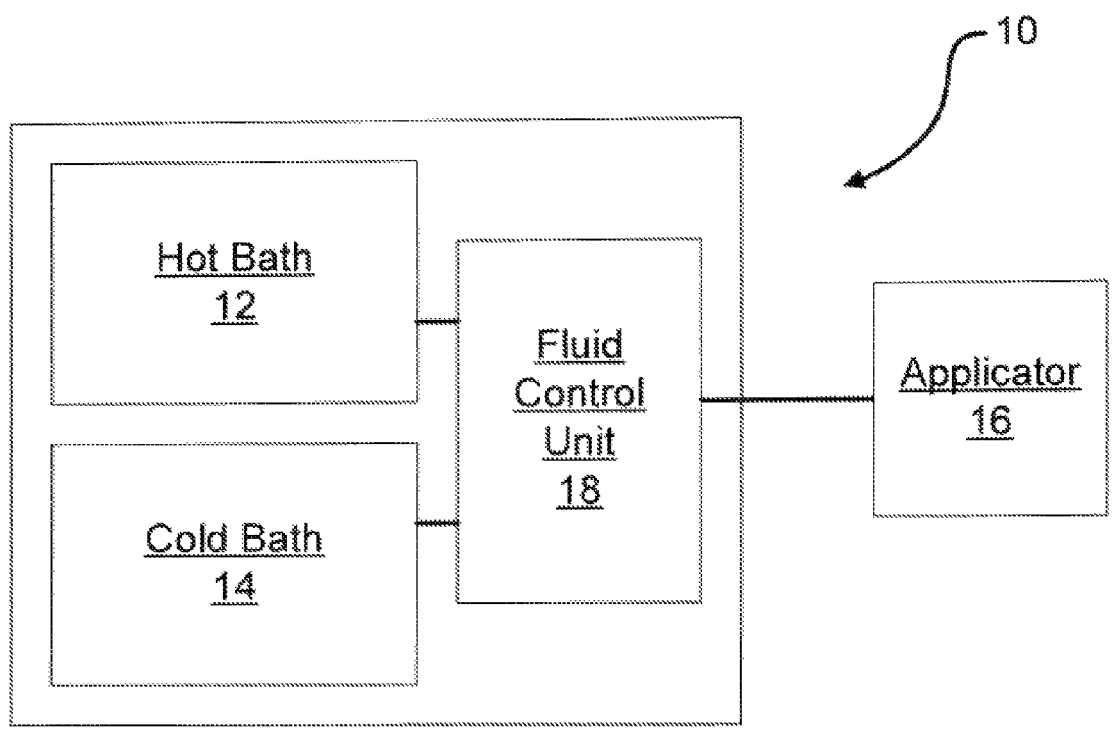
FIG. 1 is a schematic of a system for providing cooling or heating to a subject according to one embodiment of the present invention.

The term "temperature control element" refers to any structure that is able to effect an increase or reduction in temperature of an area or object of interest. A temperature control element that effects a reduction in temperature is, thus, a "cooling element." In one embodiment, the temperature control element is actively cooled or heated, as with a fluid bath or the Peltier (thermoelectric) elements that are known in the art to create cold and warm surfaces dependent upon the application of voltage. FIG. 1 shows one type of active cooling or heating system 10, comprising a hot bath 12 and a cold bath 14 in fluid communication with an applicator 16. It is understood that the term bath is not intended to limit the fluid to water. For example, the cold bath 14 could receive a fluid comprising alcohol, glycol, or mixtures of water/alcohol or water/glycol. The baths include heating or cooling means, temperature sensors, and feedback control systems to maintain selected temperatures. In one embodiment, the hot bath is about 45° C. and the cold bath is about −5° C.

Depending on the type of fluids circulated through the applicator 16, a wide temperature range can be achieved at the applicator 16. The applicator 16 can be formed from a variety of thermoconductive materials, including copper, aluminum, or alloys, and is applied to a subject's epidermis. Alternatively, the applicator 16 could be formed from a relatively thin layer of nonconductive material, such as urethane. A fluid control unit 18 is disposed between the baths and the applicator to control the applicator temperature.

Figure 2:
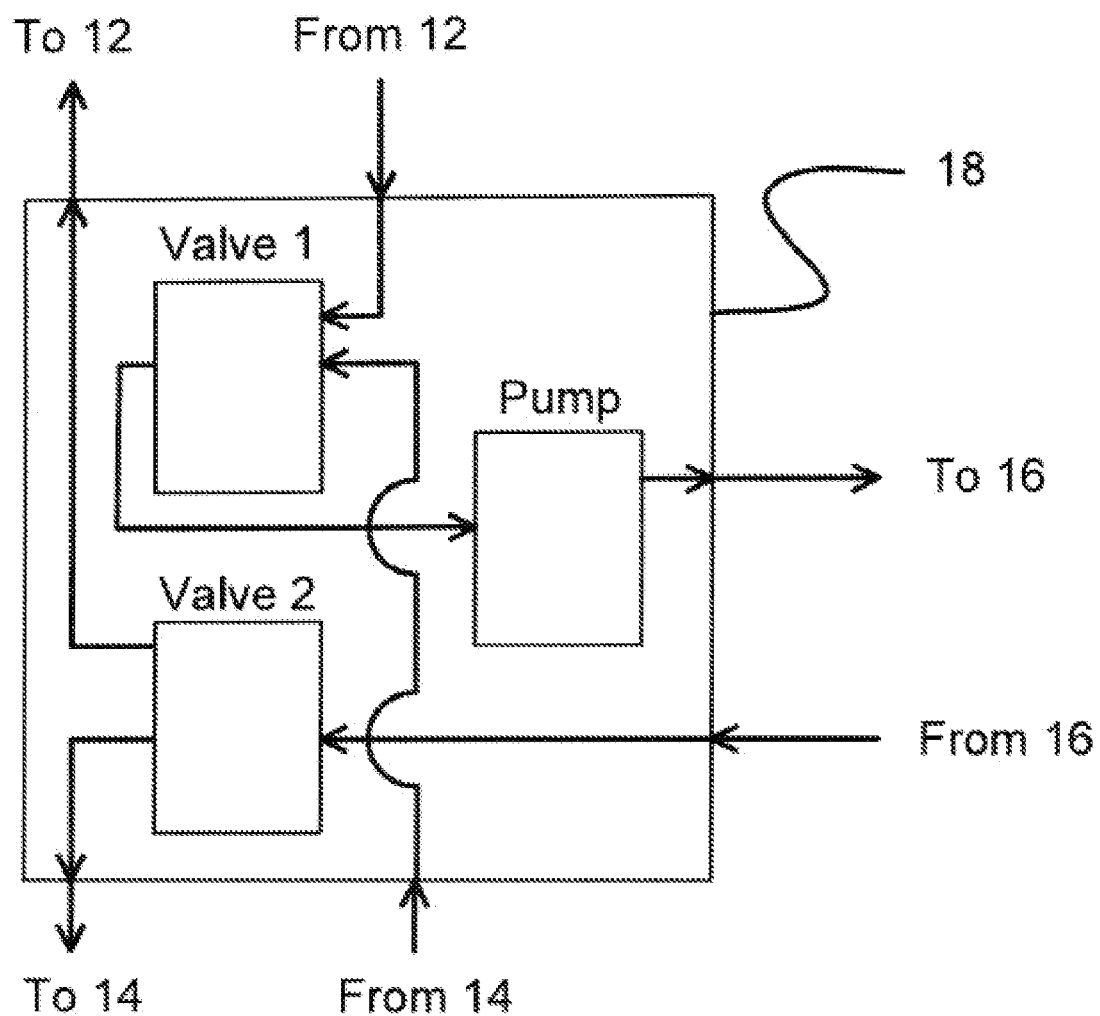
FIG. 2 is a schematic of a fluid control unit for the system of FIG. 1.

FIG. 2 provides a schematic for the fluid control unit 18, including fluid lines, a pump, a pair of valves, and logic (not depicted) for opening and closing the valves. In one embodiment, when cooling is desired, the valves route the fluid from the cold bath 14 to the pump, which circulates the fluid through the applicator and then back to the cold bath. Similarly, when heating is desired, the valves route the fluid from the hot bath 12 to the pump, which circulates the fluid through the applicator and then back to the hot bath.

Figure 3:
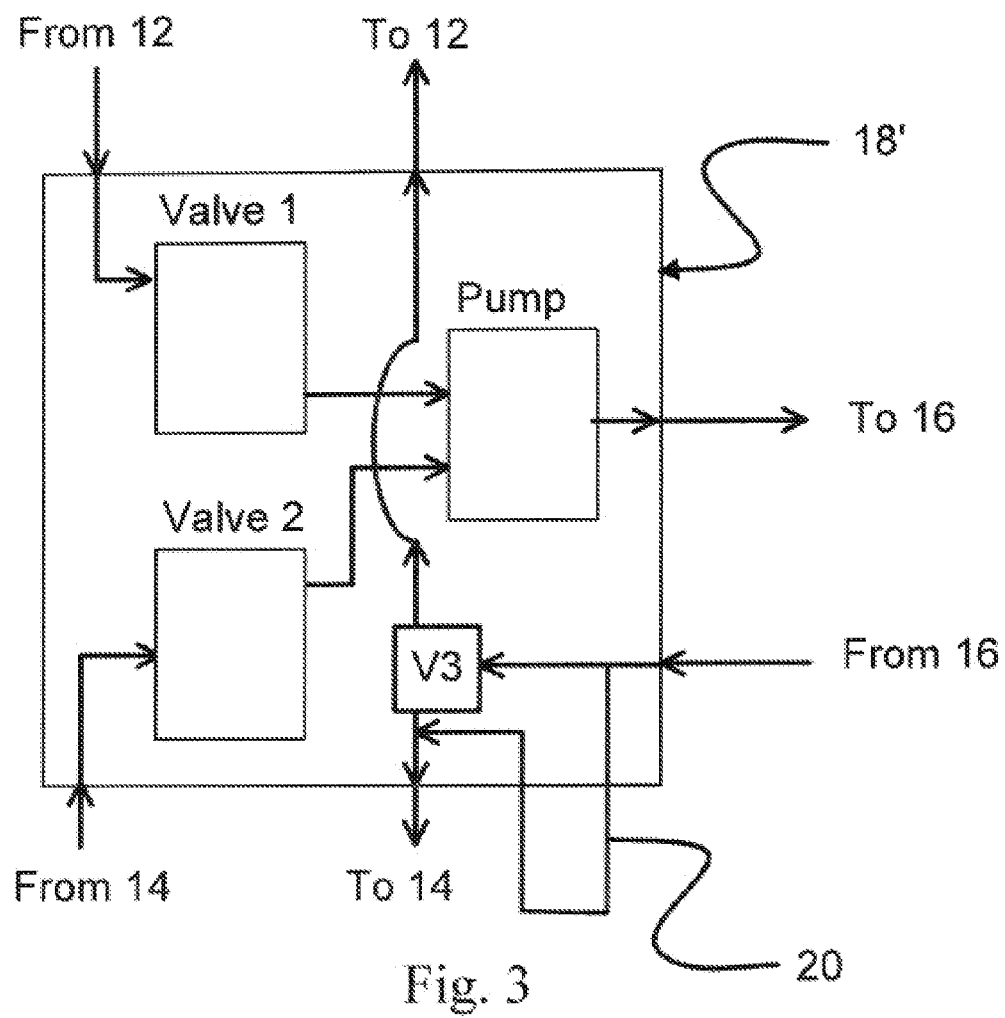
FIG. 3 is a schematic of an alternative fluid control unit for the system of FIG. 1.

Referring to FIG. 3, an alternative fluid control unit 18' is depicted, including fluid lines, a pump, three valves, and logic (not depicted) for opening and closing the valves. In one embodiment, when cooling is desired, Valve 2 is opened, while valves Valve 1 and V3 are shut. Thus, the pump draws the fluid from the cold bath 14, which circulates the fluid through the applicator 16 and then back to the cold bath through a fluid long loop 20. It is understood that fluid long loop 20 is of a sufficient length and/or diameter that when valve V3 is open, the vast majority of the fluid passes through valve V3 and out to the hot bath 12. However, when valve V3 is closed, the system pressure drives the fluid through the long loop 20 and to the cold bath 14.

Figure 4:
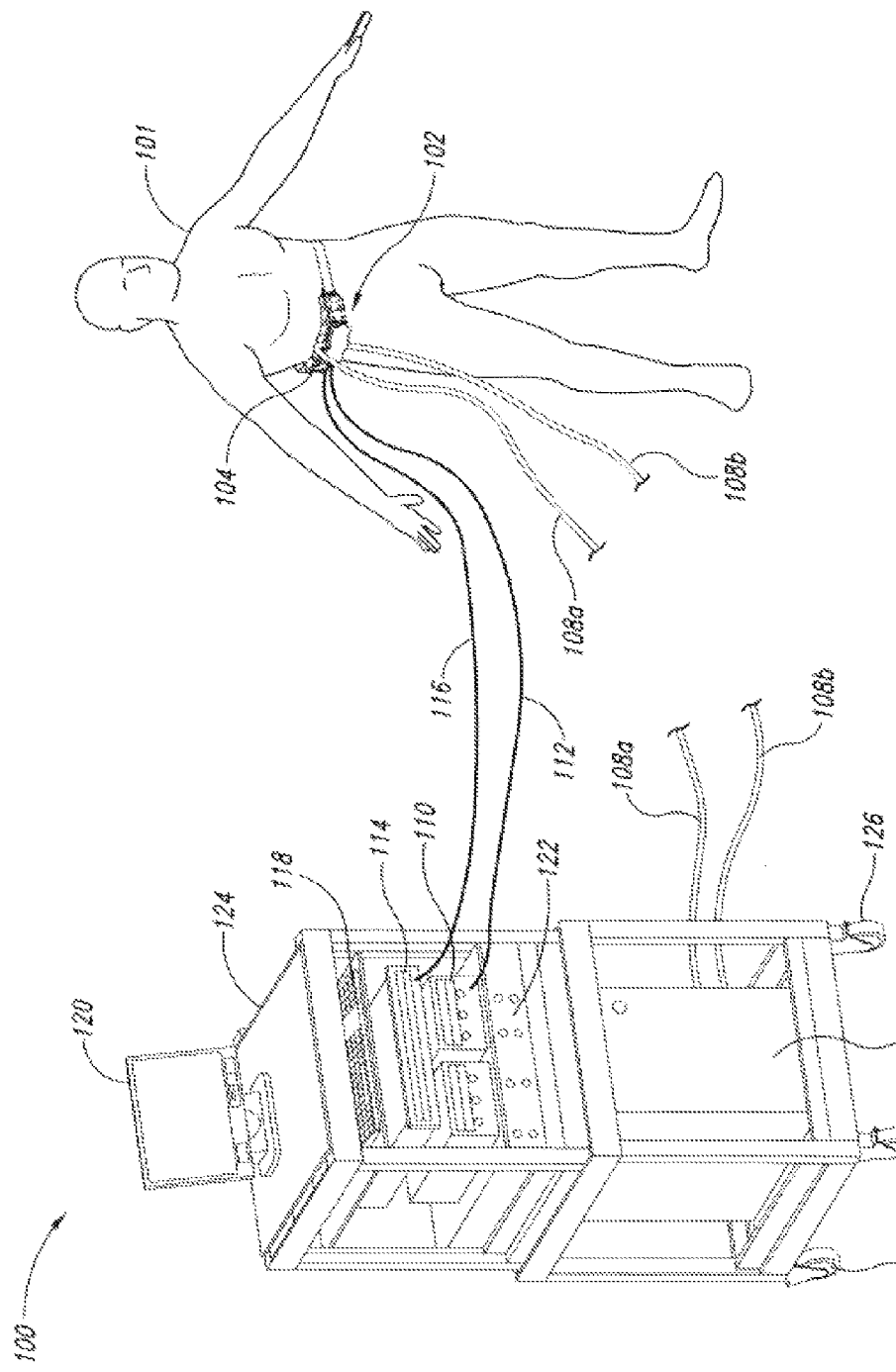
FIG. 4 shows an alternative system for providing cooling or heating to a subject.

FIG. 4 depicts another system 100 for removing heat from subcutaneous lipid-rich cells of a subject 101 in accordance with the invention. The system 100 can include a cooling device 104 placed at an abdominal area 102 of the subject 101 or another suitable area for removing heat from the subcutaneous lipid-rich cells of the subject 101.

The system 100 can further include a cooling unit 106 and supply and return fluid lines 108a-b connecting the cooling device 104 to the cooling unit 106. The cooling unit 106 can remove heat from a coolant to a heat sink and provide a chilled coolant to the cooling device 104 via the fluid lines 108a-b. Examples of the circulating coolant include water, glycol, synthetic heat transfer fluid, oil, a refrigerant, and any other suitable heat conducting fluid. The fluid lines 108a-b can be hoses or other conduits constructed from polyethylene, polyvinyl chloride, polyurethane, and other materials that can accommodate the particular circulating coolant. The cooling unit 106 can be a refrigeration unit, a cooling tower, a thermoelectric chiller, or any other device capable of removing heat from a coolant. Alternatively, a municipal water supply (i.e., tap water) can be used in place of the cooling unit.

The cooling device 104 includes a plurality of thermoelectric cooling elements, such as Peltier-type thermoelectric elements, which can be individually controlled to create a custom spatial cooling profile and/or a time-varying cooling profile. The system 100 can further include a power supply 110 and a processing unit 114 operatively coupled to the cooling device 104. In one embodiment, the power supply 110 can provide a direct current voltage to the thermoelectric cooling device 104 to effectuate a heat removal rate from the subject 101. The processing unit 114 can monitor process parameters via sensors (not shown) placed proximate to the cooling device 104 through power line 116 to adjust the heat removal rate based on the process parameters. The heat transfer rate can be adjusted to maintain constant process parameters. Alternately, the process parameters can vary either spatially or temporally. The processing unit 114 can be in direct electrical communication through line 112, or alternatively, may be connected via a wireless communication. Alternatively, the processing unit 114 can be preprogrammed to provide a spatially distributed cooling profile and/or a time-varying cooling profile. The processing unit 114 can include any processor, Programmable Logic Controller, Distributed Control System, and the like.

In another aspect, the processing unit 114 can be in electrical communication with an input device 118, an output device 120, and/or a control panel 122. The input device 118 can include a keyboard, a mouse, a touch screen, a push button, a switch, a potentiometer, and any other device suitable for accepting user input. The output device 120 can include a display screen, a printer, a medium reader, an audio device, and any other device suitable for providing user feedback. The control panel 122 can include indicator lights, numerical displays, and audio devices. In alternative embodiments, the control panel 122 can be contained on the cooling device 104. In the embodiment shown in FIG. 4, the processing unit 114, power supply 110, control panel 122, cooling unit 106, input device 118, and output device 120 are carried by a rack 124 with wheels 126 for portability. In alternative embodiments, the processing unit 114 can be contained on the cooling device 104. In another embodiment, the various components can be fixedly installed at a treatment site.

FIGS. 5-8 are isometric views of one preferred cooling device 104. In this embodiment, the cooling device 104 includes a control system housing 202 and cooling element housings 204*a-g*. The control system housing 202 includes a sleeve 308 (FIG. 9) that may slide into collar 310 and/or may mechanically attach to the cooling element housings. The cooling element housings 204*a-g* are connected to heat exchanging elements (not shown) by attachment means 206. The attachment means can be any mechanical attachment device such as a screw or pin as is known in the art. The plurality of cooling element housings 204*a-g* can have many similar features. As such, the features of the first cooling element housing 204*a* are described below with reference symbols followed by an "a," corresponding features of the second cooling element housing 204*b* are shown and noted by the same reference symbol followed by a "b," and so forth. The cooling element housing 204*a* can be constructed from polymeric materials, metals, ceramics, woods, and/or other suitable materials. The example of the cooling element housing 204*a* shown in FIGS. 5-8 is generally rectangular, but it can have any other desired shape.

Figure 5:
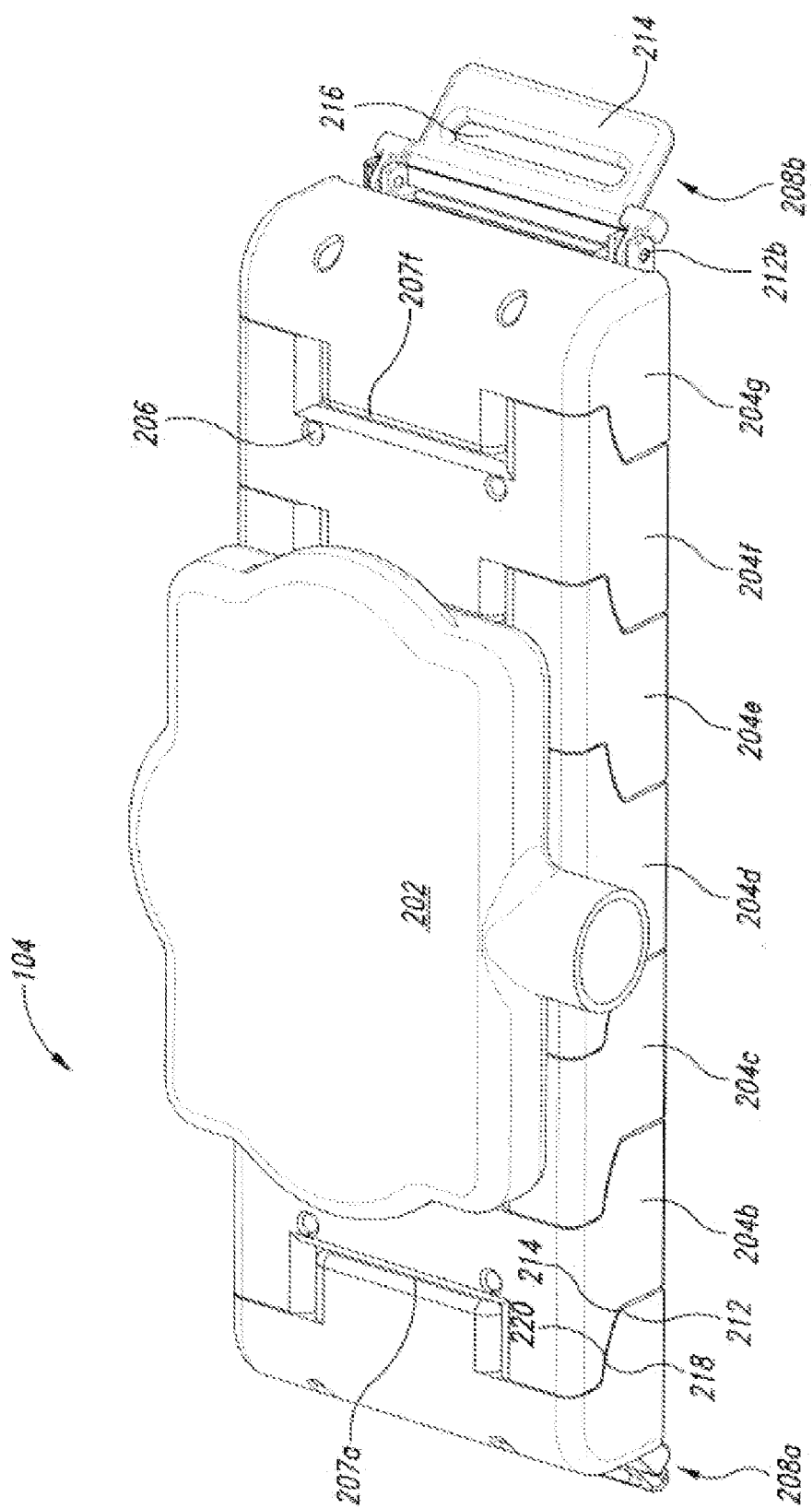
FIGS. 5-8 are isometric views of a temperature control device.
Figure 6:
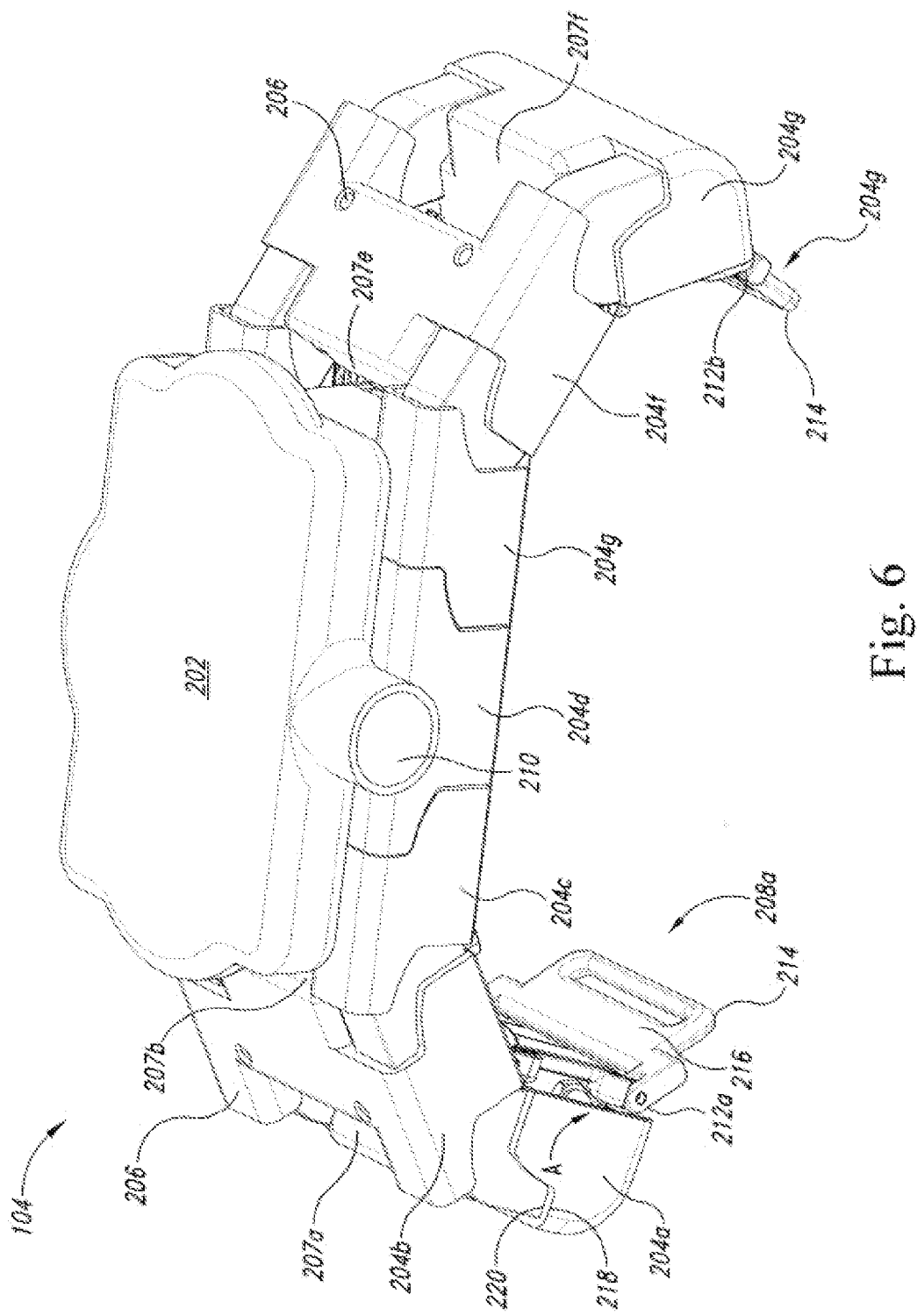
Figure 7:
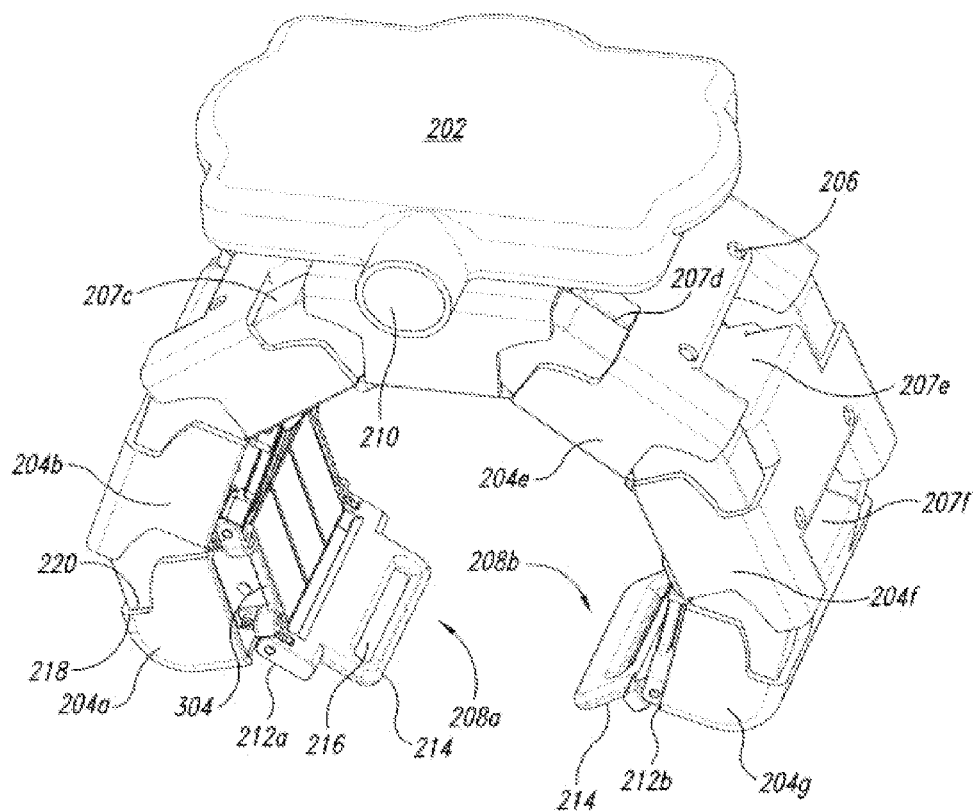

The cooling device 104 is shown in a first relatively flat configuration in FIG. 5; in a second slightly curved configuration in FIG. 6; and in a third curved configuration in FIG. 7. As shown in FIGS. 6 and 7, each segment of the cooling element housings 204*a-g* are rotatably connected to adjacent segments and moveable about connection 207*a-f* to allow the cooling device 104 to curve. The connection 207*a-f*, for example, can be a pin, a ball joint, a bearing, or other type of rotatable joints. The connection 207 can accordingly be configured to rotatably couple the first cooling element housing 204*a* to the second cooling element housing 204*b*. According to aspects of the invention, the first cooling element housing 204*a* can rotate relative to the second cooling element housing 204*b* (indicated by arrow A), each adjacent moveable pair of cooling elements being such that, for example, the angle between the first and second cooling element housings 204*a* and 204*b* can be adjusted up to a particular angle, for example 45°. In this way, the cooling device is articulated such that it can assume a curved configuration conformable to the skin of a subject.

One advantage of the plurality of rotatable heat exchanging surfaces is that the arcuate shape of the cooling device may concentrate the heat transfer in the subcutaneous region. For example, when heat exchanging surfaces are rotated about a body contour of a subject, the arcuate shape can concentrate heat removal from the skin.

The control system housing 202 can house a processing unit for controlling the cooling device 104 and/or fluid lines 108*a-b* and/or electrical power and communication lines. The control system housing 202 includes a harness port 210 for electrical and supply fluid lines (not shown for purposes of clarity). The control system housing 202 can further be configured to serve as a handle for a user of the cooling device 104. Alternatively, the processing unit may be contained at a location other than on the cooling device.

As shown in FIGS. 5-7, the cooling device 104 can further include at each end of the cooling device 104 retention devices 208*a* and 208*b* coupled to a frame 304. The retention devices 208*a* and 208*b* are rotatably connected to the frame by retention device coupling elements 212*a-b*. The retention device coupling elements 212*a-b*, for example, can be a pin, a ball joint, a bearing, or other type of rotatable joints. Alternatively, the retention devices 208*a* and 208*b* can be rigidly affixed to the end portions of the cooling element housings 204*a* and 204*g*. Alternately, the retention device can attach to control system housing 202.

The retention devices 208*a* and 208*b* are each shown as tabs 214, each having a slot 216 therein for receiving a band or elastomeric strap (not shown for purposes of clarity) to retain the cooling device 104 in place on a subject 101 during treatment. Alternatively, the cooling device may not contain any attached retention device and may be held in place by hand, may be held in place by gravity, or may be held in place with a band, elastomeric strap, or non-elastic fabric (e.g., nylon webbing) wrapped around the cooling device 104 and the subject 101.

In an alternate embodiment, the device may be a device for applying pressure, or otherwise inducing vasoconstriction, rather than a cooling device.

As shown in FIGS. 5-7, the cooling element housings 204*a-g* have a first edge 218 and an adjacent second edge 220 of a reciprocal shape to allow the cooling device 104 to mate and, thus, configure in a flat configuration. The first edge 218 and the second edge 220 are generally angular in the Figures; however, the shape could be curved, straight, or a combination of angles, curves, and straight edges that provide a reciprocal shape between adjacent segments of the cooling element housings 204*a-g*.

Figure 8:
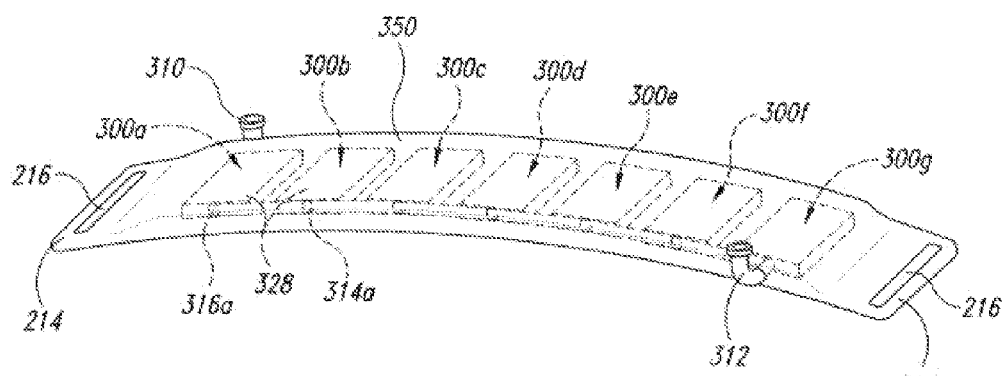
Figure 9:
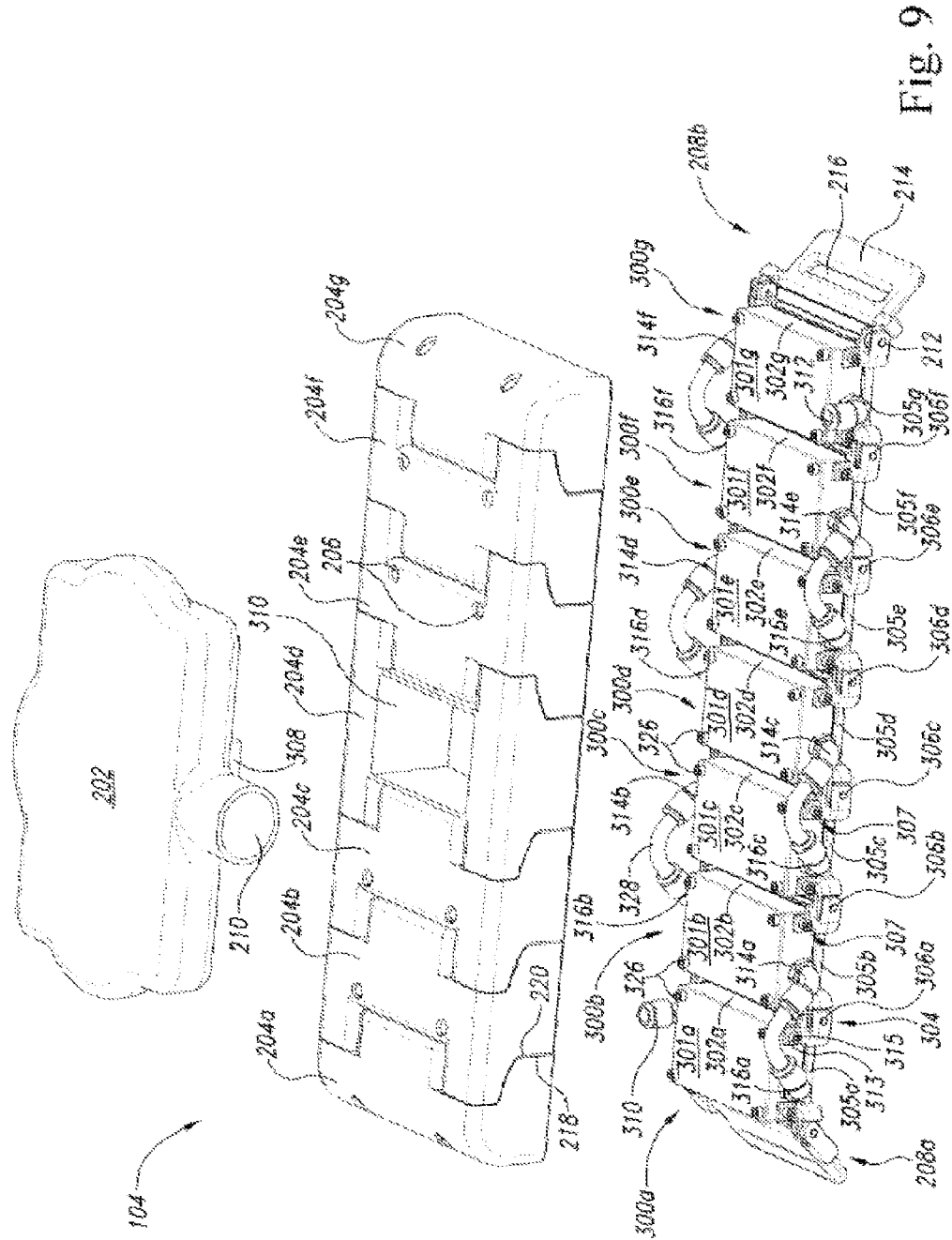
FIG. 9 is an exploded isometric view of the temperature control device of FIG. 5.

FIG. 8 shows an isometric view of an alternative cooling device 104 in accordance with embodiments of the invention suitable for use in the system 100. In this embodiment, the cooling device 104 includes a plurality of heat exchanging elements 300a-g contained within a flexible substrate 350. As described with respect to FIGS. 5-7, adjacent heat exchanging elements 300a-g are fluidly coupled in series by fluid lines 328.

The cooling elements 302a-g can be affixed to the flexible substrate 350, or may be embedded in the flexible substrate 350. The flexible substrate 350 can be constructed from polymeric materials, elastomeric materials, and/or other suitable materials. The flexible substrate 350 can further be an elastomer such as silicone or urethane or can be a fabric, such as nylon. The flexible substrate 350 can also be a thin polymer such as polypropylene or ABS. The example of the flexible substrate 350 shown in FIG. 8 is generally rectangular, but can have any other desired shape, including a matrix configuration or an anatomy specific shape.

As designed, the interface members and cooling elements protect the thermoelectric coolers while maintaining good heat transfer between the thermoelectric coolers and the skin. The interface members are sized such that they do not present a significant thermal mass. In one design, each thermoelectric cooler could be 1"×1.5". The interface member or aluminum plate could also be 1"×1.5" with a thickness of 0.04". If the thermoelectric coolers' cooling power is approximately 10 W, which is appropriate based on the heat flux expected to conduct from the skin, then the aluminum plate would cool from an ambient temperature of 20° C. to a treatment temperature of −10° C. in about 7 seconds. The change in internal energy of the plate is described by the following equation:

$$\Delta E = \rho \cdot V \cdot C \cdot \Delta T$$

where $\Delta E$ is the change in internal energy, $\rho$ is the material density, V is the material volume, C is the heat capacity of the material, and $\Delta T$ is the temperature change. In the problem described above, the volume of the aluminum plate is V=1 in×1.5 in×0.04 in or 0.06 in$^3$ (9.8×10−7 m3). For a typical grade of aluminum, C°=875 J/kg*° C. and $\rho$=2770 kg/m3. Solving the equation using these constants:

$$\Delta E = 2770 \text{ kg/m3} * 9.8 \times 10-7 \text{ m3} * 875 \text{ J/kg}*° C. *30° C. = 71.3 \text{ J}$$

If the thermoelectric coolers have a cooling power of 10 W, then 71.3 J could be removed from the aluminum plate in 7.1 seconds, as is shown in the calculation below:

$$71.3 \text{ J}/(10 \text{ J/second}) = 7.13 \text{ seconds}$$

A small gap or recess in the frame at the skin surface may be included in one embodiment. Prior to applying the cooling device to the skin, a thermally conducting fluid or coupling agent can be applied to the device and to the skin to minimize contact resistance and increase heat transfer between the cooling device and the skin. This coupling agent will fill the gap in the cooling device and allow for limited lateral conduction between the thermoelectric coolers' plates. This will create a more uniform temperature gradient across the surface area of the skin when the cooling is applied to the skin.

The lipid-rich cells can be affected by disrupting, shrinking, disabling, destroying, removing, killing, or otherwise being altered. Without being bound by theory, selectively affecting lipid-rich cells is believed to result from localized crystallization of lipids at temperatures that do not induce crystallization in non-lipid-rich cells. The crystals can disrupt or alter the bi-layer membrane of lipid-rich cells to selectively damage these cells. Thus, damage of non-lipid-rich cells, such as dermal cells, can be avoided at temperatures that induce crystal formation in lipid-rich cells. Cooling is also believed to induce lipolysis (e.g., fat metabolism) of lipid-rich cells to further enhance the reduction in subcutaneous lipid-rich cells. Vasoconstriction by means other than cooling are contemplated by the present invention. For example, pressure or administration of certain drugs may be employed to cause ischemia.

The coupling agent may be applied to the skin or to the interface member to provide improved thermal conductivity. The coupling agent may include polypropylene glycol, polyethylene glycol, propylene glycol, and/or glycol. Glycols, glycerols, and other deicing chemicals are efficient freezing-point depressants and act as a solute to lower the freezing point of the coupling agent. Propylene glycol is one exemplary component of deicer or non-freezing coupling agents. Other components include polypropylene glycol (PPG), polyethylene glycol (PEG), polyglycols, glycols, ethylene glycol, dimethyl sulfoxide, polyvinyl pyridine, calcium magnesium acetate, sodium acetate, ethanol and/or sodium formate. The coupling agent preferably has a freezing point in the range of −40° C. to 0° C., more preferably below −10° C. as further described in U.S. Provisional Application 60/795, 799, entitled Coupling Agent For Use With a Cooling Device For Improved Removal of Heat From Subcutaneous Lipid-Rich Cells, filed on Apr. 28, 2006, herein incorporated in its entirety by reference.

Figure 10:
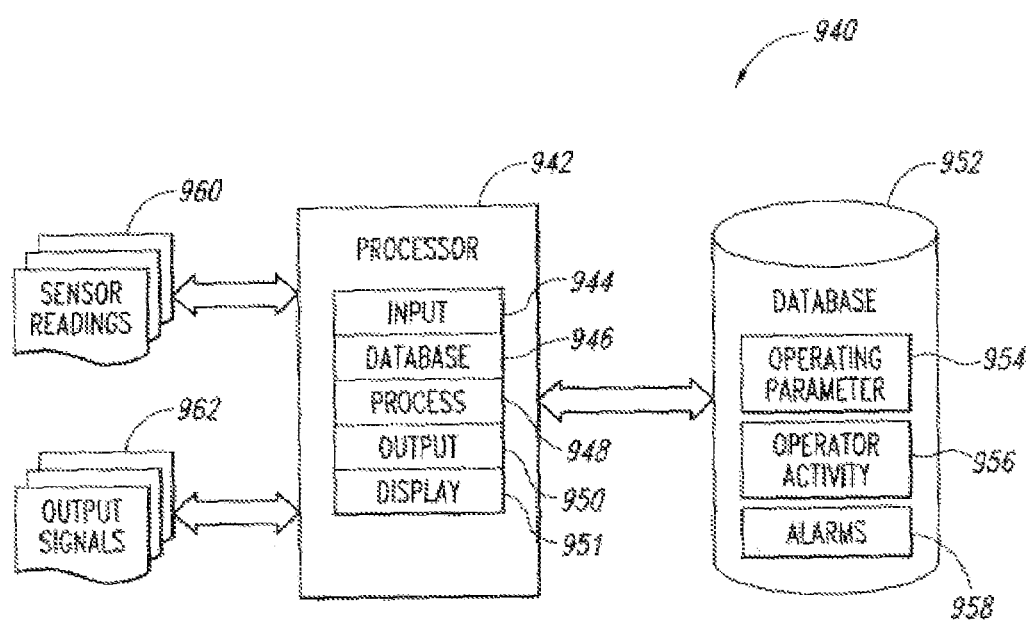
FIG. 10 is a block diagram showing computing system software modules for removing heat from subcutaneous lipid-rich cells in accordance with an embodiment of the invention.

FIG. 10 is a functional diagram showing exemplary software modules 940 suitable for use in the processing unit 114. Each component can be a computer program, procedure, or process written as source code in a conventional programming language, such as the C programming language, and can be presented for execution by the CPU of processor 942. The various implementations of the source code and object code can be stored on a computer-readable storage medium or embodied on a transmission medium in a carrier wave. The modules of processor 942 can include an input module 944, a database module 946, a process module 948, an output module 950, and, optionally, a display module 951. In another embodiment, the software modules 940 can be presented for execution by the CPU of a network server in a distributed computing scheme.

In operation, the input module 944 accepts an operator input, such as process setpoint and control selections, and communicates the accepted information or selections to other components for further processing. The database module 946 organizes records, including operating parameters 954, operator activities 956, and alarms 958, and facilitates storing and retrieving of these records to and from a database 952. Any type of database organization can be utilized, including a flat file system, hierarchical database, relational database, or distributed database, such as provided by a database vendor such as Oracle Corporation, Redwood Shores, Calif.

The process module 948 generates control variables based on sensor readings 960, and the output module 950 generates output signals 962 based on the control variables. For example, the output module 950 can convert the generated control variables from the process module 948 into 4-20 mA output signals 962 suitable for a direct current voltage modulator. The processor 942 optionally can include the display module 951 for displaying, printing, or downloading the sensor readings 960 and output signals 962 via devices such as the output device 120. A suitable display module 951 can be a video driver that enables the processor 942 to display the sensor readings 960 on the output device 120.

One interesting feature of a thermoelectric cooler is that if the polarity of the applied voltage is reversed, the cold side becomes warm and the warm side becomes cold. In this way, the thermoelectric cooler may be employed to increase the blood flow rate and stimulate reperfusion in the cooled tissue. This would cause ischemia-reperfusion injury and improve the results achieved by the methods described in U.S. Patent Publication No. 2003/0220674 and in U.S. Patent Publication No. 2005/0251120.

Regardless of the cooling element type, the cooling element can be maintained at an average temperature between about −30° C. and about 35° C., preferably from about −20° C. to about 20° C., more preferably from about −20° C. to about 10° C., more preferably from about −15° C. to about 5° C., more preferably from about −10° C. to about 0° C. In one embodiment, the region is exposed to the cooling element from about 2 min to about 60 min, or preferably from about 5 min to about 30 min.

After cooling has been effected or vasoconstriction otherwise induced, the tissue of interest is exposed to an energy source to increase blood flow. The term "energy source" refers to any known form of energy that would increase blood flow in a subject, either by inflammation or other mechanisms. As will be recognized, the energy source can be the same device used to effect cooling (as, for example, by changing the temperature profile of a fluid bath or by reversing polarity on the applied voltage of a thermoelectric cooler) or a different device. Energy sources according to the invention can supply electromagnetic energy (e.g., light, radiofrequency), thermal energy (e.g., heat) and/or mechanical energy (e.g., physical contact, friction, vibration, sound waves). In preferred embodiments, the energy source causes the blood flow rate to increase more rapidly than would occur without the energy source.

The energy source can, for example, be a capacitively coupled RF device such as those in which a power source provides energy to an RF generator and then to at least one RF electrode. An electronic measuring system measures current, voltage, and temperature via thermal sensors. The present invention utilizes an electronic measuring system driven by a controller, such as a computer with appropriate software. Various feedback or monitoring systems attached to the controller include ultrasonic, thermal, or impedance monitors. Current and voltage are used to calculate impedance. The output for these monitors is used by the controller to control the delivery of RF power. The amount of RF energy delivered controls the amount of RF power.

In one embodiment, the RF energy is provided by an RF electrode coated with dielectric material. The use of dielectric coating produces a more uniform impedance throughout the electrode and causes a more uniform current to flow through the electrode. The resulting effect minimizes edge effects around the edges of the electrode. It is desirable to have the electrical impedance of the dielectric layer to be higher than that of the subject tissue. In various embodiments, the impedance of layer 32' at the operating frequency, can be in the range of 200 Ω/cm² or greater. Suitable materials for a dielectric coating include, but are not limited to, TEFLON, silicon nitride, polysilanes, polysilazanes, polyimides, KAPTON, antenna dielectrics and other dielectric materials well known in the art.

In one embodiment, one or more RF electrodes are connected to an RF generator. The temperature of the tissue or of RF electrode is monitored, and the output power of energy source adjusted accordingly. The system can be a closed- or open-loop system to switch power on and off, as well as modulate the power. A closed-loop system utilizes a microprocessor to serve as a controller to monitor the temperature, adjust the RF power, analyze the result, feed back the result, and then modulate the power. More specifically, a controller governs the power levels, cycles, and duration that the radiofrequency energy is distributed to the individual electrodes to achieve and maintain power levels appropriate to achieve the desired treatment. In one embodiment, the controller is an INTEL PENTIUM microprocessor; however it will be appreciated that any suitable microprocessor or general purpose digital or analog computer can be used to perform one or more of the functions of controller.

With the use of sensor and feedback control system skin or other tissue adjacent to the RF electrode can be maintained at a desired temperature for a selected period of time without causing a shut-down of the power circuit to electrode due to the development of excessive electrical impedance at electrode or adjacent tissue. Current and voltage can be measured by sensors, and used to calculate impedance and power. A control signal is generated by controller that is proportional to the difference between an actual measured value, and a desired value. The control signal is used by power circuits to adjust the power output in an appropriate amount in order to maintain the desired power delivered at respective RF electrodes.

In a similar manner, temperatures detected at a sensor provide feedback for maintaining a selected power. A control signal is generated by a controller that is proportional to the difference between an actual measured temperature and a desired temperature. The control signal is used by power circuits to adjust the power output in an appropriate amount in order to maintain the desired temperature delivered at the sensor.

Examples of methods utilizing RF on a subject are disclosed in U.S. Pat. No. 6,413,255 and U.S. Pat. No. 5,948,011, the entire disclosures of which are incorporated herein.

Alternatively, the energy source can be vibrational, and delivered by a conventional vibrating device. Such vibratory massagers are known to increase blood circulation and perfusion. Representative devices include the Endermologie ES1 device (LPG Systems, Valence, France), VelaSmooth system (Syneron Inc, Richmond Hill, Ontario, Canada), and TriActive Laserdermology system (Cynosure Inc, Chelmsford, Mass., USA).

Alternatively, the energy source can be acoustic, and delivered by ultrasound transducers. Ultrasound energy is well known to those skilled in the art to be capable of heating tissue. Treatment devices can include a high intensity focused ultrasound (HIFU) system—in particular, a system with a plurality of independently controlled multiple beam transducer elements that are capable of being focused at the treatment depths below the skin surface. A HIFU transducer comprises an array of transducer elements. Each transducer element comprises a piezoelectric element, solid coupling element, and focusing lens. The transducer elements may span treatment depths including 0.35 to 3.5 cm. For example, five transducer elements may have focal points of 0.5, 0.8, 1.2, 1.9, and 3.0 cm, with correspondingly operate frequencies of 12, 9, 7, 5.5, and 4 MHz, respectively. It should be noted that the transducer may comprise different numbers of transducer elements.

The HIFU transducer supplies a predetermined amount of ultrasonic energy per unit distance traveled (not per unit time) for each treatment region and sensors that detect cavitation and boiling of the fat tissue. The HIFU transducer can be controlled to determine the desired temperature through feedback mechanisms. For example, a monitored Doppler dynamic sound caused by cavitation or boiling may be used as an indicator to set a power level outputted by the transducer in the HIFU system. Examples of methods utilizing HIFU on a subject are disclosed in U.S. Patent Publication No. 2006/0122509, U.S. Patent Publication No. 2005/0154431, and U.S. Patent Publication No. 2004/0039312, the entire disclosures of which are incorporated herein.

In one embodiment, the energy source is applied such that the region is warmed to about normal body temperature. Alternatively, the energy source is applied such that the region is warmed to above normal body temperature. Alternatively, the energy source is applied such that the region is warmed to a temperature warmer than the temperature of the previously cooled lipid-rich cells, at least enough to stimulate reperfusion.

The amount of time that the energy source is applied typically depends on the energy source itself. For example, depending on the source, the energy is applied for from about 1 sec to about 30 min. Preferably, the energy is applied for from about 1 sec to about 15 min. Skilled artisans are aware of the variables to consider when applying energy to a subject.

In certain embodiments, energy, such as capacitively coupled radiofrequency energy, is applied to the tissue with energy of about 10 J/cm$^2$ to about 1000 J/cm$^2$ is applied to the tissue. Preferably, about 50 J/cm$^2$ to about 300 J/cm$^2$ is applied to the tissue.

Free radical-mediated mechanisms of cellular damage are believed to be involved after periods of ischemia and reperfusion. Nishikawa, *Ultrastructural Changes and Lipid Peroxidation in Rat Adipomusculocutaneous Flap Isotransplants after Normothermic Storage and Reperfusion*, Transplantation, Vol. 54, 795-801, 1992. More particularly, it is known that fat has a greater predisposition to free radical damage than skin. *Id*; Coban, *Ischemia-Reperfusion Injury of Adipofascial Tissue: An Experimental Study Evaluating Early Histologic and Biochemical Alterations in Rats, Mediators of Inflammation*, Vol. 5, 304-308, 2005 (fat tissue is more susceptible to ischemic events). These studies look to minimize injury to fat tissue during transplants. By contrast, while not intending to be bound by theory, it is believed that it is beneficial to augment ischemia-reperfusion injury in the adipose tissue, thus enhancing adipose tissue necrosis.

The damage of reperfusion injury is due in part to the inflammatory response of damaged tissues. White blood cells carried to the area by the newly returning blood release a host of inflammatory factors such as interleukins as well as free radicals in response to tissue damage. The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. Redox signaling is the concept that free radicals, reactive oxygen species (ROS), and other electronically-activated species act as messengers in biological systems. Leukocytes may also build up in small capillaries, obstructing them and leading to more ischemia.

In certain embodiments, the methods of the invention further comprise treating the region to encourage formation of oxygen radicals. Oxygen radicals are damaging to tissues, and their concentration may be increased in a number of ways, including locally administering oxygen radical forming compounds (such as bleomycin) and compounds (such as the interleukins and other immune adjuvants) that stimulate inflammation by, for example, stimulating release of inflammatory mediators and/or leukocyte activity. In yet another embodiment, the method further comprises treating the region to encourage formation of intracellular and/or extracellular ion concentrations at other than normal levels.

The present invention provides methods of treating subcutaneous adipose tissue in a region of a subject's body, comprising exposing said region to a cooling element under conditions effective to cool said tissue; and stimulating reperfusion in the cooled tissue by exposing the tissue to an energy source to increase the blood flow rate to the cooled tissue. In one embodiment, stimulating reperfusion in the tissue causes ischemia-reperfusion injury to the tissue. Ischemia-reperfusion injury in the tissue permanently damages adipocytes present in the tissue.

In some embodiments, the methods further comprise determining the amount of adipocytes present in the tissue. The determination may be made before the exposing step, after the exposing step, or both before and after the exposing step.

In another embodiment, the present invention provides methods of treating subcutaneous adipose tissue in a region of a subject's body, comprising exposing said region to a cooling element under conditions effective to cool said tissue; and causing an ischemia-reperfusion injury to the cooled tissue by exposing the tissue to an energy source to increase the blood flow rate to the cooled tissue.

In the foregoing specification, the concepts have been described with reference to specific embodiments. Many aspects and embodiments have been described above and are merely exemplary and not limiting. After reading this specification, skilled artisans appreciate that other aspects and embodiments are possible without departing from the scope of the invention. Moreover, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause the same to occur or become more pronounced are not to be construed as a critical, required, or essential feature of any or all the claims.

It is to be appreciated that certain features are, for clarity, described herein in the context of separate embodiments, but may also be provided in combination in a single embodiment. Conversely, various features that are, for brevity, described in the context of a single embodiment, may also be provided separately or in any subcombination. Further, reference to values stated in ranges include each and every value within that range.

What is claimed:

1. A method for selective reduction of lipid-rich cells in a region of a human subject's body, comprising:
    treating the region to encourage formation of oxygen radicals by locally administering an oxygen radical forming compound;
    exposing an epidermal layer in said region to a cooling element under conditions effective to cool subcutaneous adipose tissue in said region; and
    increasing a rate of blood flow to the cooled tissue by exposing the region to an energy source.

2. The method of claim 1, further comprising cycling at least one of the steps of exposing said region to a cooling element and increasing blood flow.

3. The method of claim 1, further comprising the step of increasing vasoconstriction.

4. The method of claim 1, wherein the energy source causes the blood flow rate to increase more rapidly than would occur without the energy source.

5. The method of claim 1, wherein the cooling element is maintained at an average temperature between about −20° C. and about 5° C.

6. The method of claim 1, wherein the epidermal layer in said region is exposed to the cooling element from about 2 min to about 60 min.

7. The method of claim 1, wherein the cooling element includes a thermoelectric cooling element.

8. The method of claim 1, wherein the cooling element includes a cooling agent circulating through the cooling element.

9. The method of claim 1, wherein the energy source provides at least one of thermal, vibrational, acoustic, and electromagnetic energy.

10. The method of claim 1, wherein the energy source provides mechanical energy.

11. The method of claim 1, wherein the energy source is applied such that the region is warmed to at least about normal body temperature.

12. The method of claim 1 wherein the energy source is applied such that the region is warmed to a temperature warmer than the temperature of the cooled tissue.

13. The method of claim 12 wherein the region is warmed sufficient to stimulate reperfusion.

14. The method of claim 1, wherein the energy is applied for from about 1 sec to about 30 min.

15. The method of claim 1, wherein energy of about 10 J/cm2 to about 1000 J/cm2 is applied to the tissue.

16. The method of claim 1, wherein the steps produce ischemia-reperfusion injury.

17. The method of claim 1, further comprising treating the region to encourage formation of intracellular and/or extracellular ion concentrations at other than normal levels.

18. A method of treating subcutaneous adipose tissue in a region of a subject's body, comprising:
   treating the region to encourage formation of oxygen radicals by locally administering an oxygen radical forming compound;
   exposing said region to a cooling element under conditions effective to cool said tissue; and
   stimulating reperfusion in the cooled tissue by exposing the region to an energy source to increase the blood flow rate to the cooled tissue.

19. The method of claim 18, wherein stimulating reperfusion in the tissue causes ischemia-reperfusion injury to adipocytes in the tissue.

20. The method of claim 18, wherein the energy source causes the blood flow rate to increase more rapidly than would occur without the energy source.

21. A method of treating subcutaneous adipose tissue in a region of a subject's body, comprising:
   treating the region to encourage formation of oxygen radicals by locally administering an oxygen radical forming compound;
   exposing said region to a cooling element under conditions effective to cool said tissue; and
   causing an ischemia-reperfusion injury to the cooled tissue by exposing the region to an energy source to increase the blood flow rate to the cooled tissue.

22. A method for selective reduction of lipid-rich cells in a region of a human subject's body, comprising:
   treating the region to encourage formation of oxygen radicals by locally administering an oxygen radical forming compound;
   selectively causing vasoconstriction in adipose tissue; and
   subsequently stimulating reperfusion by applying an energy source to thereby increase blood flow to the region.

23. The method of claim 22 wherein the step of causing vasoconstriction is by applying pressure.

24. The method of claim 22 wherein the step of causing vasoconstriction is by administration of drugs.

25. A method for selective reduction of lipid-rich cells in a region of a human subject's body, comprising:
   treating the region to encourage formation of oxygen radicals by locally administering an oxygen radical forming compound;
   selectively creating ischemia in lipid-rich cells in a region of a human subject's body; and
   subsequently stimulating reperfusion by applying an energy source to thereby increase the blood flow.

* * * * *